United States Patent
Aguilar

[11] Patent Number: 5,902,278
[45] Date of Patent: May 11, 1999

[54] HYPODERMIC SYRINGE

[76] Inventor: David G. Aguilar, 1371 Prospect Ave., Long Beach, Calif. 90804

[21] Appl. No.: 08/898,145

[22] Filed: Jul. 22, 1997

Related U.S. Application Data

[63] Continuation of application No. 08/754,684, Nov. 21, 1996, abandoned.

[51] Int. Cl.$^6$ ...................................................... A61M 5/00
[52] U.S. Cl. ........................................... 604/227; 604/187
[58] Field of Search .................................. 604/227, 187, 604/218, 228

[56] References Cited

U.S. PATENT DOCUMENTS

| | | | |
|---|---|---|---|
| 794,190 | 7/1905 | Schneyder . | |
| 1,589,046 | 6/1926 | Brix . | |
| 2,585,815 | 2/1952 | McClintock | 128/218 |
| 2,593,757 | 4/1952 | Hofacker | 128/264 |
| 2,842,128 | 7/1958 | Hein | 128/218 |
| 3,316,909 | 5/1967 | Cowley | 128/218 |
| 3,380,450 | 4/1968 | Adelberger | 128/218 |
| 3,384,082 | 5/1968 | Harrold | 128/218 |
| 3,640,278 | 2/1972 | Friedman | 128/218 |
| 3,943,926 | 3/1976 | Barragan | 128/218 |
| 4,060,083 | 11/1977 | Hanson | 128/223 |
| 4,217,896 | 8/1980 | Behnke | 128/218 |
| 4,324,241 | 4/1982 | Reese | 128/218 |
| 4,664,128 | 5/1987 | Lee | 128/753 |

FOREIGN PATENT DOCUMENTS

| | | | |
|---|---|---|---|
| 332766 | 2/1921 | Germany | 604/227 |

OTHER PUBLICATIONS

Sherwood Medical Catalog, pp. A–4, G–3; "Needles & Syringes, Biopsy and I.V." Section, p. 11; "Anesthesia, Respiratory, Suction" section, p. 6.

*Primary Examiner*—John D. Yasko
*Attorney, Agent, or Firm*—Lyon & Lyon LLP

[57] ABSTRACT

Disclosed is an ergonomically improved hypodermic syringe which facilitates one-handed use by allowing the same hand that holds the syringe to operate the plunger conveniently to accomplish both the distal (injecting) stroke and the proximal (aspirating) stroke. The syringe includes a pair of finger-stop structures on diametrically opposite sides of the barrel which block slippage in both proximal and distal directions and which do not occupy the barrel's entire circumference and do not interfere with the legibility of a calibration scale that passes through the region of the barrel with which said structures are associated. A loop atop the syringe's plunger member is also provided, which is adjustable to vary the size of the aperture thereof for a snug fit with fingers and thumbs of varying sizes. In combination, the adjustable loop and finger-stops make the syringe plunger easily operable in both directions with one hand. The result is a syringe which is inexpensive to manufacture, which is compact to store and ship, and which enables an aspiration maneuver, to test for the presence of blood indicating that a blood vessel has been penetrated, to be performed easily with one hand.

4 Claims, 4 Drawing Sheets

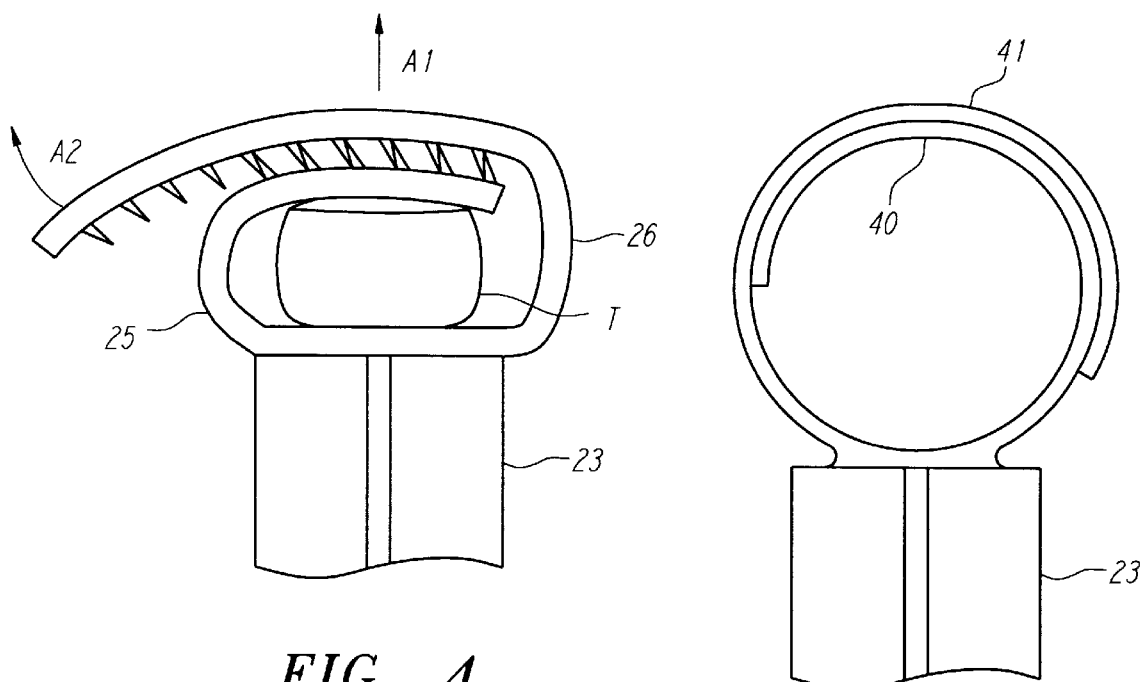
FIG. 4
FIG. 5
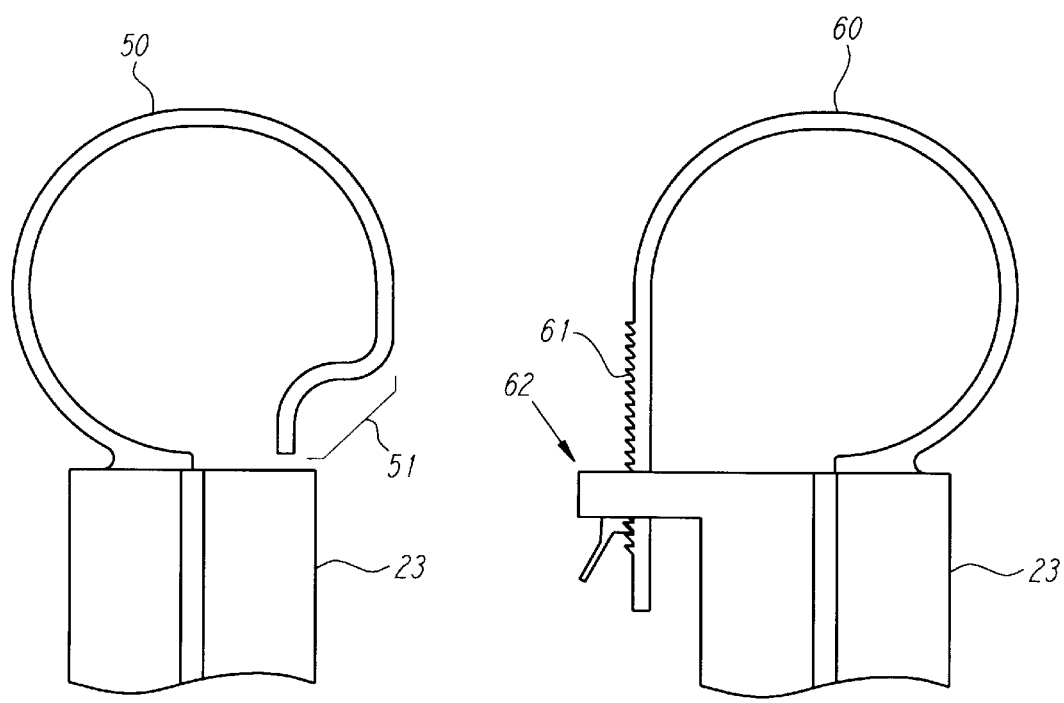
FIG. 6
FIG. 7

HYPODERMIC SYRINGE

This is a continuation of application Ser. No. 08/754,684, filed Nov. 21, 1996 now abandoned.

BACKGROUND OF THE INVENTION

The field of the present invention is hypodermic syringes. The invention has particular application to those hypodermic syringes which are used for administering medicaments such as vaccines, local anesthetics and antibiotics which are designed to be injected intramuscularly, subcutaneously, or intradermally but not directly into a vein or artery. The invention also has particular application to those hypodermic syringes which are used in introducing catheters and tubes into the lumens of blood vessels. The present invention is directed to certain improvements in the construction of a hypodermic syringe which facilitate one-handed performance of an aspiration test, hereinafter further described, which is useful to avoid the accidental injection of medicaments into blood vessels or else to confirm that the tip of the needle is in the lumen of a blood vessel when this is the desired goal, as in catheterizing a blood vessel. The improvements are ones which are suitable for incorporation into a fully disposable, single-use syringe of compact size and configuration which has barrel and plunger components that can be made of moldable plastics.

Correct technique for injecting medicaments which are intended for hypodermic but not intravenous injection requires the practitioner to insert the syringe needle into muscle, subcutaneous or intradermal tissue and then draw back on the plunger and observe whether blood is or is not aspirated into the syringe barrel. If the practitioner observes blood being aspirated, the practitioner takes this as an indication that the needle has perforated a vein or artery, and the needle is then withdrawn and the injection procedure started over at a different site. Performance of this so-called aspiration test is recommended in numerous guides and treatises which physicians and other clinical professionals regularly consult. For example, a well-known nursing training text includes this instruction: "Aspirate by holding the barrel of the syringe steady with your nondominant hand and by pulling back on the plunger with your dominant hand. If blood appears in the syringe, withdraw the needle, discard the syringe, and prepare a new injection. Rationale: This step determines whether the needle is in a blood vessel." (B. Kozier & G. Erb, *Fundamentals of Nursing Concepts and Procedures* [3d Ed., Addison-Wesley 1987], p. 1521.) Another well-known nursing treatise, in instructing on how to administer a subcutaneous injection, recommends the aspiration step "to determine whether the needle is in a blood vessel" and warns that "[d]iscomfort and possibly a serious reaction may occur if a drug intended for subcutaneous use is injected into a vein." (L. Wolf, M. H. Weitzel & E. Fuerst, *Fundamentals of Nursing* [6th Ed., J. B. Lippincott 1979], p. 614). Similarly, a *Physicians' Desk Reference* (hereinafter cited simply as "PDR") article on Haemophilus b Conjugate (Tetanus Toxoid Conjugate) reconstituted with CLI DTP (Diphtheria, Tetanus and Pertussis) vaccine warns that the vaccine is not to be injected intravenously and recommends: "After insertion of the needle, aspirate to ensure that the needle has not entered a blood vessel." (R. Arky, medical consultant, *Physicians' Desk Reference* [49th Ed., Medical Economics Data Prod. Co. 1995], p. 903.) In addition to the cited references, there are numerous others which recommend that the aspiration test be performed to minimize risk of unintentionally injecting medicaments into blood vessels.

It is noted in the medical literature that failure to perform the aspiration test, resulting in the accidental injection into a blood vessel of a medicament not intended for that mode of administration, may have serious consequences for the patient. For example, in L. Tessio, L. Bassi and L. Strada, *Spinal Cord Lesion After Penicillin Gluteal Injection*, 6 Paraplegia 442 (June 1992), the authors state that in eight cases seen by or reported to them, gluteal injection of penicillin caused sudden and irreversible paraplegia. The authors suggest that "the mechanism might be the accidental injection into the superior gluteal artery, causing its distal spasm and the upstream ascent of the penicillin with ensuing embolic and/or spastic occlusion of the anterior spinal artery." For another example, it is noted in J. R. Roberts & J. R. Hedges, *Clinical Procedures in Emergency Medicine* [Saunders 1985], p. 436, that there is risk of inducing convulsions and generalized seizures in patients by injecting local anesthetics (intended for intramuscular or subcutaneous administration) into an artery by mistake.

As for vaccines, there is apparently little or no published evidence of toxicity to the patient resulting from accidental injection into a blood vessel. However, for absorption reasons, vaccines are typically designed to be injected intramuscularly or subcutaneously, and immunogenicity from vaccines can depend on proper administration. Hence, there is at least reason for concern that a vaccine intended for intramuscular or subcutaneous injection might not have the same efficacy if injected into a vein or artery, even if no toxicity to the patient would thereby result. (In addition to the PDR article cited above regarding the Haemophilus b Conjugate (Tetanus Toxoid Conjugate) reconstituted with CLI DTP (Diphtheria, Tetanus and Pertussis) vaccine, PDR articles pertaining to other vaccines as well caution that they are not to be injected intravenously. See, e.g., articles on the Measles, Mumps and Rubella Virus Vaccine, PDR, p. 1575, and on the Hepatitis B Vaccine, id., p. 2372).)

Although reports of adverse effects on patients from accidental injections of medicaments into blood vessels are apparently not common, the severity of possible risks dictates that the aspiration test should be performed routinely, whenever an intramuscular, subcutaneous or intradermal injection of a medicament is administered.

In most clinical settings involving normal adult patients, the drawing-back-the-plunger maneuver, and hence the aspiration test, can be accomplished without any intolerable amount of difficulty because the patient can ordinarily be relied upon to hold still voluntarily. The practitioner thus has both hands free, and so can grasp the barrel of the syringe in one hand while drawing back the plunger with the other hand to check for aspiration of blood. Even with normal adults, however, there are clinical situations (such as, for example, the injection of a local anesthetic into a painful area) in which the need to use one hand to immobilize the injection site, leaving the practitioner with only one hand free to operate the syringe, poses serious inconvenience to a practitioner trying to perform the aspiration test.

Where the patient is a child, performance of the drawing-back-the-plunger maneuver is especially likely to prove cumbersome and inconvenient with a conventional syringe. Children, in contrast to normal adults, often struggle when receiving injections, and cannot be depended upon to possess the self-control necessary to hold still voluntarily. Hence, a practitioner who is, for example, injecting a medicament into the arm of a child must take steps to see that the child's arm is held immobile during the injection. Otherwise there is risk of such mishaps as the practitioner's suffering an accidental needle stick, or breaking off the needle in the patient's arm, or accidentally withdrawing the entire needle, or lacerating the patient's tissue. Unless the practitioner has an assistant to hold the child, the practitioner must typically hold the child's arm immobile with one hand while operating the syringe with the other hand. The practitioner therefore does not have two hands free to accomplish the drawing-back-the plunger maneuver; and with a syringe of the kind now conventionally used for the intramuscular, subcutaneous or intradermal injection of vaccines, antibiotics and other medicaments, the maneuver is very difficult, if not altogether impossible, to perform with one hand. The result is that the practitioner is tempted to, and all too often does, forego the drawing-back-the-plunger maneuver, omit the aspiration test, and hence fail to make certain that a vein or artery has not been perforated by accident. Correct technique, and its attendant advantages in terms of safety and efficacy, are thereby sacrificed for convenience's sake.

There are clinical situations where the practitioner, rather than desiring to avoid perforating a blood vessel, desires instead to confirm that such perforation has been accomplished. One example of such a situation is when the practitioner desires to accomplish a venous catheterization, that is, the introduction of a catheter, or tube, into the lumen of a vein. Such catheterization may be desired, for example, in order to secure intravenous access for delivery of medicaments or in order to guide a sensing device. to the patient's heart to take cardiac measurements. Typically, catheterization is accomplished by first inserting a relatively large-bore hypodermic needle through a vein, often without a syringe attached. When the practitioner believes that the needle has achieved the through-the-vein position, a syringe containing saline is attached and, while the practitioner withdraws the plunger in an aspirating maneuver, he or she simultaneously begins a gradual withdrawal of the syringe and needle. The practitioner looks for aspirated blood to appear in the syringe, indicating that the tip of the needle has now been withdrawn to the point where it is in the lumen of the vein. With the needle so positioned, the practitioner detaches the syringe and introduces a guidewire into the vein through the bore of the needle. The needle is then slipped out over the guidewire and a catheter is slipped in over the guidewire. Once the catheter is in place the guidewire is withdrawn through the catheter. A syringe is then attached to the catheter and an aspiration stroke is typically performed, the appearance of aspirated blood in the syringe being a reconfirmation that the catheter is correctly positioned in the lumen of the vein. The syringe typically is then used to flush the catheter with heparin to inhibit formation of clots and emboli.

The venous catheterization technique just described depends, of course, on the practitioner's success in positioning the tip of the needle within the lumen of the vein; and the aspiration-while-gradually-withdrawing-the-needle maneuver is important in that it confirms that that positioning has been achieved. Syringes according to the present invention, because they render it ergonomically easier than conventional syringes to accomplish the aspiration stroke while handling the syringe with a single hand, enhance the ease and convenience with which the practitioner can accomplish the aspiration-while-gradually-withdrawing-the-needle maneuver.

So-called "control syringes" are known in the art which include a pair of finger rings affixed to opposite sides of the barrel (the barrel rings), together with a thumb ring atop the plunger. By inserting the index and middle fingers through the barrel rings and the thumb through the thumb ring, the practitioner can achieve a measure of control over the syringe and can operate the plunger on the backward (withdrawing) stroke with one hand. However, the three-rings arrangement of the "control syringe" is typically seen in a syringe much larger than syringes designed for the intramuscular injection of medicaments and syringes designed for use in venous catheterization procedures. "Control syringes" are typically not intended for those uses, but instead for irrigation and the like.

It would not be immediately apparent or obvious to adapt the three-rings feature of the "control syringe" to provide a one-hand-operable syringe for the intramuscular injection of medicaments, because the resulting syringe would have substantial obvious disadvantages. First, the barrel rings, being relatively large and bulky, would increase material cost, would increase the complexity of molding the syringe body if it were attempted to mold it in a single piece, and would make the syringe less compact to package, ship and store. While making the syringe barrel itself larger might make it easier to attach and configure the rings, the use of an unnecessarily large disposable syringe would make for unnecessary cost and waste of materials, and could also make difficult the accurate measurement of doses as small as some doses, especially pediatric doses, can be (e.g., 0.5 cc or the like). Thus, syringe designers would not consider such a design to be acceptable. Secondly, the manual maneuver required to insert the fingers through the barrel rings would be slow and awkward compared to the simpler maneuver of grasping the barrel of the syringe between the fingers (or between finger and thumb) in the region of the finger-stops of the present invention as hereinafter described. Thirdly, neither the barrel rings nor the thumb ring on a conventional "control syringe" are adjustable, but are instead made in fixed diameters designed to admit the largest fingers and thumbs expected to be encountered. Practitioners with average or smaller than average sized fingers will find their grasp of a control syringe to be less than optimally secure because of the looseness, or play, which results from the excessive size of the rings. Fourthly, the non-adjustable ring atop the plunger of a control syringe, necessarily being designed to accommodate the largest normal thumb, will be much too large to make a snug fit with a small or even a normal index finger inserted therethrough; whereas the adjustable plunger loop of the present invention, as hereinafter described, affords equal convenience to those practitioners who choose to operate the plunger with the index finger while grasping the barrel between the thumb and middle finger (as is typical in administering vaccines) and those practitioners who prefer to operate the plunger with the thumb while grasping the syringe barrel between the index and middle fingers (as is typical in administering local anesthetics).

SUMMARY OF THE INVENTION

The present invention provides an improved hypodermic syringe for the intramuscular, subcutaneous or intradermal injection of vaccines, antibiotics, anesthetics and other medicaments, and for the catheterization of blood vessels. The improvements are designed to encourage the practitioner, when inserting medicaments not intended for intravenous delivery, to perform the aspiration test by making it easy and convenient to operate the syringe on the backward (plunger-withdrawing) stroke with a single hand, thereby to observe whether or not blood is aspirated into the syringe, indicating that a blood vessel has been perforated and that the needle should be withdrawn and the injection procedure started over. The improvements also make the syringe of the present invention more easily usable in procedures involving the catheterization of blood vessels.

The improvements, because they facilitate one-handed performance of the aspiration test, make the syringe especially desirable for injecting pediatric patients, for injecting patients in areas where it is cumbersome to have two hands on the syringe, and in general for injecting patients who, because of tremors, convulsive disorders or other reasons, cannot or will not hold still for an injection and require the practitioner to use one hand to stabilize the injection site while using the other hand, alone, to operate the syringe.

The hypodermic syringe of the present invention is preferably of the fully disposable type, having a barrel molded from plastic in a single piece and a plunger member also molded from plastic in a single piece, fitted at the distal end thereof with a conventional piston that cooperates with the bore of the barrel in the conventional way. The barrel is provided at the distal end with a conventional hub on which is mounted (preferably detachably) a conventional hollow needle. The plunger member is fitted at the proximal end with a loop that can be adjusted to embrace, snugly but easily releasably, a variety of sizes of fingers and thumbs when inserted therethrough. At diametrically opposed positions upon the exterior surface of the barrel, and preferably molded integrally therewith, is a pair of finger-stop structures which serve as barriers such that when the barrel is grasped in the region of the finger-stop structures between the index and middle fingers (or between the middle finger and thumb, if the index finger is being used to operate the plunger), the fingers grasping the barrel are not only prevented from slipping in the proximal (rearward) direction along the barrel during the forward (injection) stroke of the plunger but are also prevented from slipping in the distal (forward) direction along the barrel during the backward (aspiration) stroke of the plunger. The finger-stop structures are preferably not fully circumferential about the barrel, and preferably are so positioned as not to interfere with the legibility of a calibration scale which is inscribed longitudinally upon the barrel and which extends into, or through, that region of the barrel with which the finger-stop structures are associated.

Thus it is an object of the present invention to provide a hypodermic syringe that is ergonomically well adapted to the structural and functional limitations of the human hand, such that the syringe is easily operable, both on the backward (aspiration) and forward (injection) stroke, with but a single hand.

It is a further object of the present invention to provide an improved hypodermic syringe that promotes safe and sound injection technique by facilitating performance of the aspiration test in patients, such as pediatric patients and persons with tremors and convulsive disorders, who typically will not, or cannot, voluntarily hold still while being injected.

It is a further object of the present invention to promote the safe, rapid and efficient administration of intramuscularly, subcutaneously or intradermally injected medicaments to large numbers of patients, especially children, by enabling a single practitioner properly to inject them without the help of an assistant to hold the patients.

It is a further object of the present invention to provide a disposable hypodermic syringe for the intramuscular, subcutaneous or intradermal injection of medicaments whose body and plunger member are each moldable in a single piece.

Yet a further object of the present invention is to provide a disposable hypodermic syringe which is convenient for one-handed use in injecting local anesthetics.

Still another object of the present invention is to provide a disposable hypodermic syringe for the intramuscular, subcutaneous or intradermal injection of medicaments which is compact in its dimensions, thereby to conserve space in its packaging, shipping and storage and to conserve materials in its manufacture.

An additional object of the present invention is to provide a syringe which promotes ease and efficiency in accomplishing venous catheterization, in that it facilitates performance of the above-described aspiration-while-gradually-withdrawing-the-needle maneuver, and the above-described aspirating-blood-through-the-catheter maneuver, with a single hand.

Other purposes, advantages and objects of the present invention will appear from the description that follows, including the drawings which are parts hereof.

BRIEF DESCRIPTION OF THE DRAWINGS

FIG. 4 is a detailed plan view of the proximal end of the plunger assembly, showing the adjustable plunger loop of FIG. 3 with its aperture closed about a finger (or thumb) which has been inserted therethrough and secured therein.

FIG. 5 is a detailed plan view of another alternative embodiment of an adjustable plunger loop having two loop members which define an aperture through which a finger (or thumb) can be inserted to be held securely therein.

FIG. 6 is a detailed plan view of another alternative embodiment of an adjustable plunger loop, having a single loop member which defines an aperture through which a finger (or thumb) can be inserted to be held securely therein.

FIG. 7 is a detailed plan view of another alternative embodiment of an adjustable plunger loop, having a single loop member which defines an aperture through which a finger (or thumb) can be inserted to be held securely therein, the size of said aperture being adjusted by drawing the free end of the loop member through a ratchet housing.

DETAILED DESCRIPTION OF THE PREFERRED EMBODIMENTS

Figures 1, 2, 3:
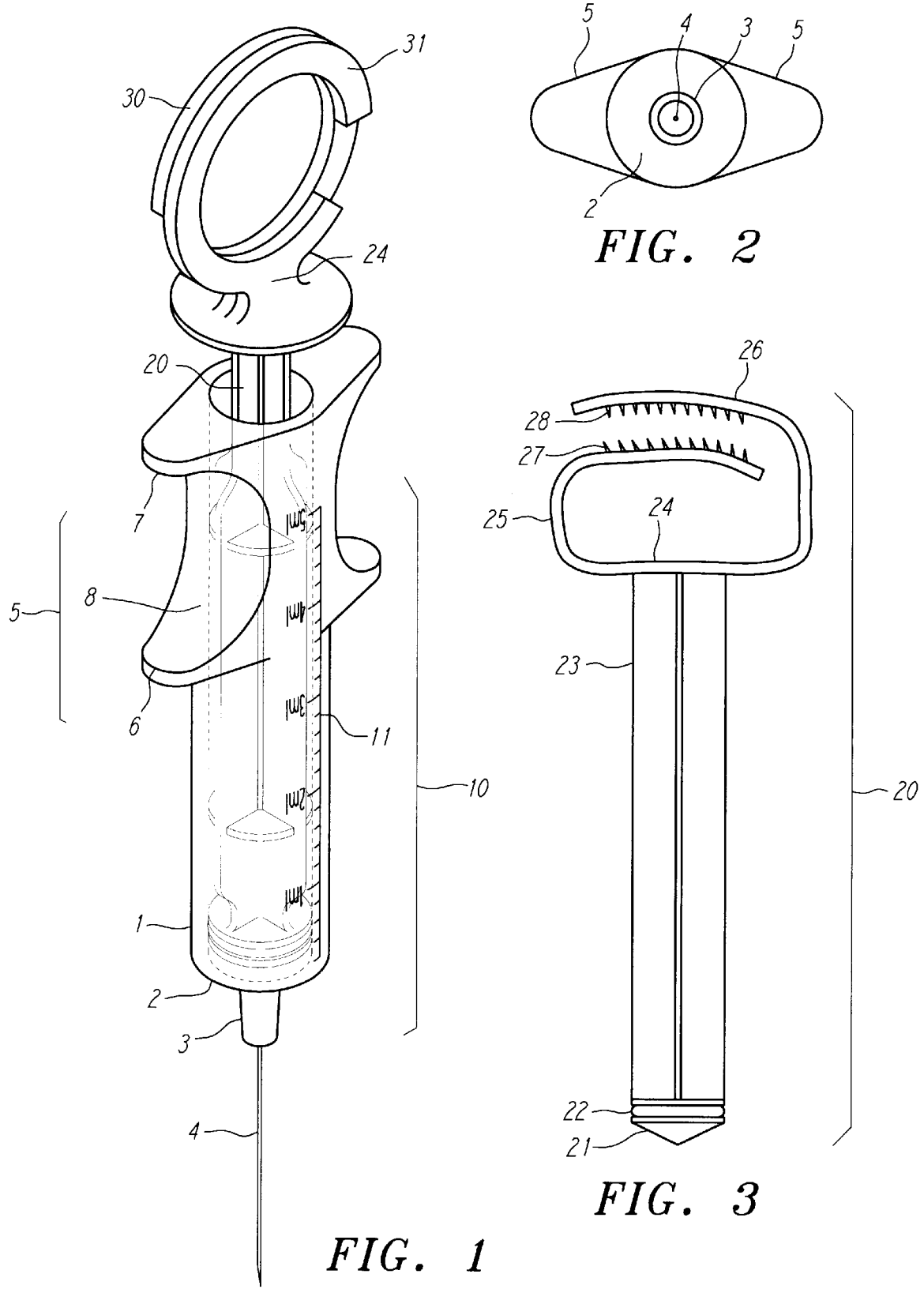
FIG. 1 is a perspective view of a hypodermic syringe illustrating a preferred embodiment of the invention.
FIG. 2 is a view along the longitudinal axis of the syringe body, from the distal end. It illustrates the diametrically opposed positions of two finger-stop structures on the exterior surface of the syringe barrel.
FIG. 3 is a plan view of the plunger member of a hypodermic syringe according to the present invention, having at its distal end a conventional piston and at its proximal end on alternative embodiment of a plunger button with two loop members formed integrally therewith which, when closed together, define the aperture of an adjustable plunger loop.

The syringe of the present invention, a preferred embodiment of which is illustrated in FIG. 1, includes a body 10 having a barrel portion 1 which outwardly is generally configured as a right circular cylinder for most of its length and has a frusto-conical portion 2 near the distal end, where the body diameter reduces down to the diameter of a conventional hub 3, upon which is mounted (preferably detachably) a conventional hollow needle 4. The body 10 includes a hollow bore (shown in phantom) which is open at the proximal end to receive a plunger member 20. The bore within the barrel portion of the syringe body is generally configured, according to convention, as a right circular cylinder so dimensioned that the plunger shaft 23, with the piston 21 at its distal end, fits closely but slidably therein. The syringe body 10 is preferably made of moldable plastic in a single piece, but any of a number of other materials would also be suitable, including for example glass or metal, and the body could be made in multiple pieces which could then be fused, cemented or otherwise joined together by conventional means.

Figure 10:
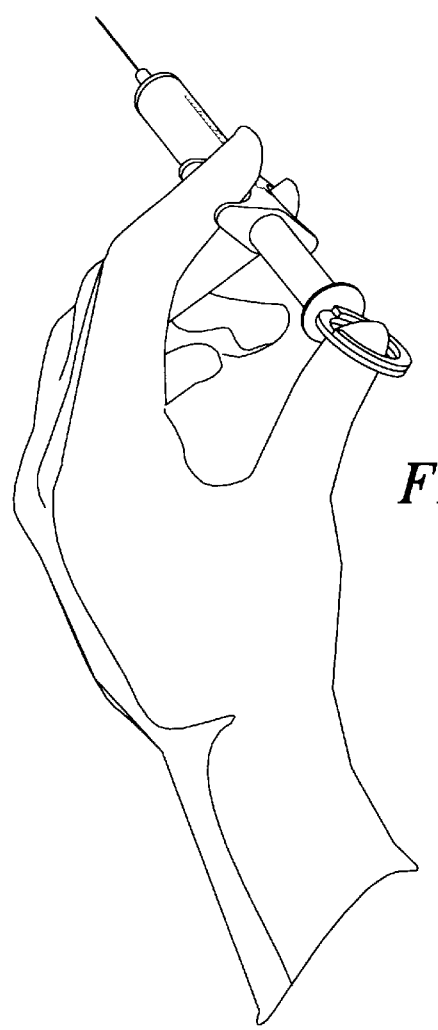
FIG. 10 is a perspective view showing the syringe barrel being grasped between the index and middle fingers of a hand while the thumb is poised to operate the plunger, as is typical when the syringe is being used to inject a local anesthetic.
Figure 11:
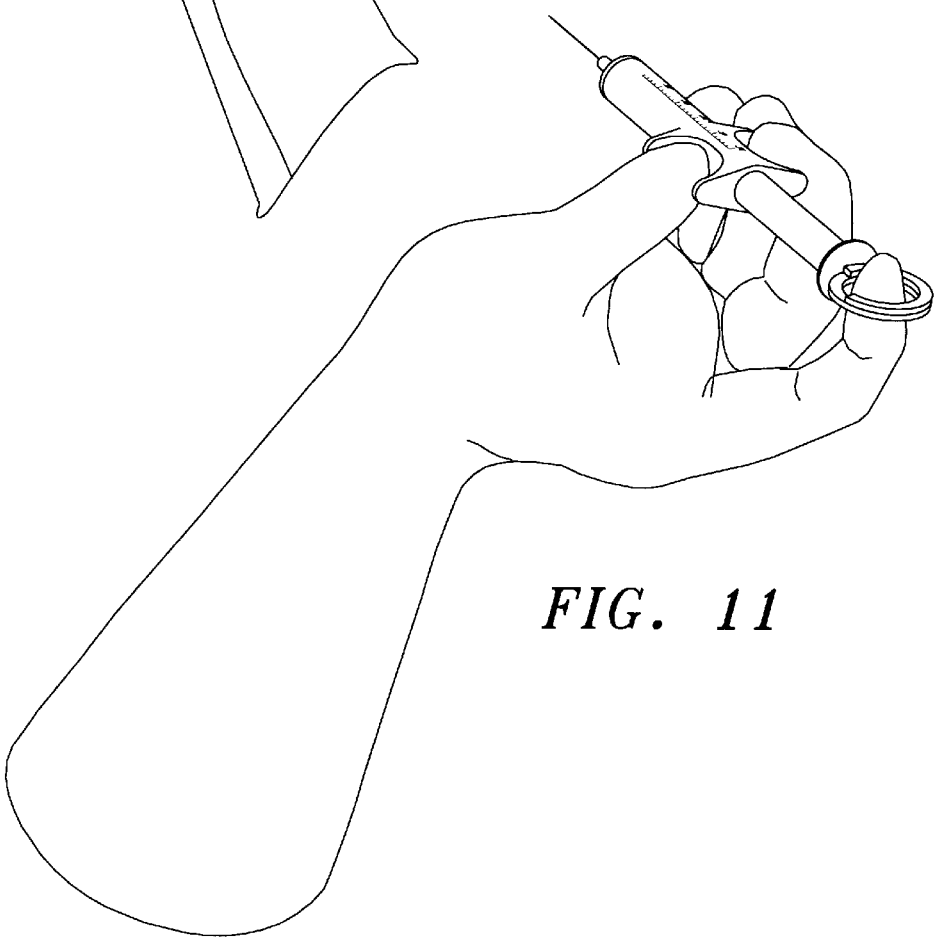
FIG. 11 is a perspective view showing the syringe barrel being grasped between the thumb and the middle finger of a hand while the index finger is poised to operate the plunger, as is typical when the syringe is being used to inject a vaccine.

On the barrel portion 1 of the syringe body 10, at diametrically opposed positions, is a pair of finger-stop structures 5, 5. In the preferred embodiment shown in FIGS. 1 and 9, each of the finger-stop structures has a distal barrier 6 and a proximal barrier 7 which define a region 8 therebetween, which region 8 is sufficiently wide and deep to accommodate an adult finger or thumb, so that the syringe barrel can easily be grasped in region 8 between the index and middle fingers (if the practitioner chooses to operate the plunger with the thumb as shown in FIG. 10) or between the middle finger and thumb (if the practitioner chooses to operate the plunger with the index finger as shown in FIG. 11). When the syringe barrel is grasped in region 8 between said fingers (or between said finger and thumb), slippage of the fingers down the barrel in a distal direction is blocked by the distal barrier 6, while slippage up the barrel in a proximal direction is blocked by the proximal barrier 7. Thus the finger-stops are dual-directional: They impede slippage of the barrel-grasping fingers in both the distal and the proximal direction. In this they differ from the flange often seen at the proximal end of a conventional molded syringe barrel, which flange is designed to block slippage of the fingers in the proximal direction only.

The finger-stop structures 5, 5 need not be positioned at the extreme proximal end of the syringe body 1, but may be positioned longitudinally at some intermediate place between the proximal and distal ends of the barrel portion 1 of the syringe body 10. The finger-stop structures preferably are molded integrally with the rest of the syringe body 10, as this avoids the extra manufacturing steps of separately making the finger-stop structures and of affixing them to the barrel; but they can be made separately and affixed by conventional means such as bonding by heat or any suitable glue or cement.

Figure 9:
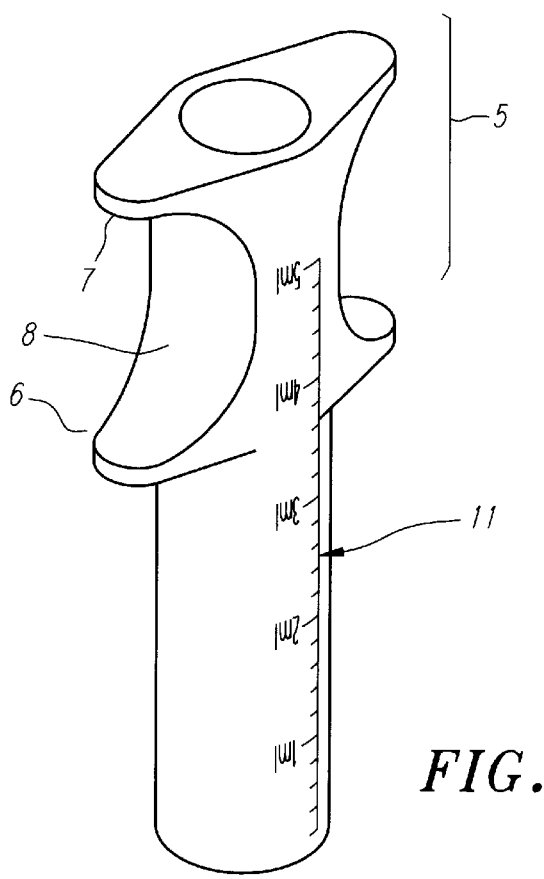
FIG. 9 is a perspective view of a portion of the barrel of a syringe made according to the present invention, showing a pair of finger-stop structures at diametrically opposed positions on the external surface of the barrel, and a calibration scale affixed longitudinally upon the barrel and extending into the longitudinal region of the barrel where the finger-stop structures are located, but at a radially different position such that the finger-loop structures do not interfere with the legibility of the calibration scale.

As is most clearly seen in FIGS. 1, 2, 9 and 11, the finger-stop structures 5, 5 do not occupy the entire circumference of the barrel in the longitudinal region thereof at which they are placed. Instead they leave part of that circumference unobstructed, so that a calibration scale 11 can be inscribed longitudinally along the barrel continuously without hindrance or interruption, and without compromise to its legibility where the calibration scale passes into or through the longitudinal region of the barrel at which the finger-stop structures are placed. As is best seen in FIGS. 1 and 9, the calibration scale does enter the longitudinal region where the finger-stop structures are, but the calibration scale occupies a different radial position than do the finger-stop structures, thus avoiding interference. This arrangement affords the practical advantage of avoiding unduly lengthening the barrel, as would be necessary if the entirety of the calibration scale had to be located distally of the finger-stop structures. Unnecessary barrel length is undesirable for several reasons, including these: It compromises the goal of compactness of packaging, storage and shipping of the syringes, a consideration particularly important in disposable syringes, which are typically sold and used in large quantities and as to which the costs associated with packaging, shipping and storage are typically a more important consideration than with syringes designed to be reused; it requires more material to manufacture a longer syringe barrel (and a longer plunger assembly to cooperate with the longer barrel), thus increasing cost and waste; and a longer barrel requires greater length of travel of the plunger during the stroke, making the syringe less easily controllable and the plunger member ergonomically harder to operate in both directions with one hand.

It will be appreciated that finger-stop structures much different from those shown in FIGS. 1, 2 and 9 may be used instead. Any pair of structures formed upon, attached to or impressed into diametrically opposed places on the barrel may serve the purpose of dual-directional finger-stops as long as those structures serve to inhibit slippage of the syringe-holding fingers in both the proximal and the distal direction along the barrel. Among the alternative structures that could be employed as finger-stops at diametrically opposed places on the barrel are, for example, the following: Patches of knurled, scored or otherwise roughened surface upon the exterior of the barrel; dimples or depressions or other concavities in the exterior surface of the barrel; or a pair of parallel, interrupted rings occupying a portion of the circumference of the barrel. Even a single such interrupted ring, if located at a suitable longitudinal position intermediate between the proximal and distal ends of the barrel (such as at region 8 indicated in FIGS. 1 and 9), would serve as an adequate dual-directional finger-stop, although some convenience would be sacrificed by the operator's need to perform a grip-shifting maneuver in transitioning from the upward (aspiration) stroke to the downward (injection) stroke; that is, the syringe-grasping fingers would have to be positioned above (i.e., proximally from) the single interrupted ring so that it would serve as a barrier against slippage in the distal direction during the upward (aspiration) stroke but then shifted to a position below ((i.e., distally from) the ring so that it would serve as a barrier against slippage in the proximal direction during the downward (injection) stroke of the plunger.

As seen in FIG. 3, the plunger member 20 includes at its distal end a piston 21, preferably made of rubber or other resilient material and preferably having at least one ring 22 which, when the plunger shaft 23 is inserted into the bore, forms a seal with the wall thereof which is impermeable to liquids and gases. At the proximal end of the plunger shaft 23 is a plunger button 24, having associated therewith an inferior loop member 25 and a superior loop member 26. The loop members are preferably made of a flexible plastic material and are preferably integrally molded with plunger button 24, which in turn is preferably integrally molded with plunger shaft 23.

Upon the superior surface of inferior loop member 25, and preferably molded integrally therewith, are a series of whisker-like projections 27. It will be appreciated that they do not project perpendicularly from the surface of said inferior loop portion, but at a slightly backward slant with reference to the distal end thereof. A corresponding series of whisker-like projections 28 is formed on the inferior surface of the superior loop member 26. If desired, the inferior loop member 25 may be biased upwardly and the superior loop member 26 biased downwardly, so that in the structure's resting state the superior surface of inferior loop member 25 bears against the inferior surface of superior loop member 26, causing whisker-like projections 27 to engage the whisker-like projections 28. Alternatively, the two loop members may be biased so that they are spaced apart, as seen in FIG. 3, but may be urged together to form a closed aperture which is tightened around, and securely holds, a finger or thumb inserted therethrough, as seen in FIG. 4.

It will be appreciated that when the whisker-like projections 27 and 28 are engaged with each other, they cooperate in a ratchet-like manner, such that the loop aperture which loop members 25 and 26 define can be made smaller by sliding the superior loop member 26 distally (leftwardly in FIG. 3), but the structure resists sliding in the opposite direction. Hence, the whisker-like projections cause the superior and inferior loop members to cooperate with each other in such a manner that the loop aperture can easily be made smaller but will resist being made larger when the whisker-like projections 27 and 28 are engaged with each other.

As can best be seen in FIG. 4, superior loop member 26 can be closed down upon inferior loop member 25 and, either by pulling superior loop member 26 in its distal (i.e., leftward, in FIG. 4) direction or by pinching together the left and right sides of the loop formed by loop members 25 and 26, a finger or thumb T can be snugly embraced within the loop aperture formed by the cooperation of said loop members. As can readily be seen, the two loop members may be slipped and slid with respect to each other so as to adjust the size of the aperture they form, thereby to accommodate a variety of differently-sized fingers and thumbs, making the loop adjustable to accommodate different practitioners' different finger sizes, and to accommodate each practitioner's personal preference whether to operate the plunger with the index finger or with the thumb.

It will also be appreciated that when the finger or thumb T exerts force upwardly in the direction indicated by arrow A1 in FIG. 4, as it would if the finger or thumb T were being used to withdraw the plunger from the syringe barrel, as in performing the aspiration test, the whisker-like projections 27, 28 will be pressed forcibly against each other, causing the loop aperture to resist opening. When the injection procedure is completed, finger or thumb T can be easily released simply by lifting up the distal end of superior loop member 26 in the direction of arrow A2, shown in FIG. 4, thereby disengaging the whisker-like projections 27, 28 from each other and permitting the opening of the loop aperture and the easy release of the thumb or finger held within that aperture. Alternatively, the finger or thumb may simply be withdrawn from the aperture of the loop without opening the loop. Hence, an adjustable and easily releasable plunger loop is provided which serves to facilitate one-handed performance of the aspiration step.

As should be apparent from the foregoing description, whisker-like projections 27, 28 function as means for fastening loop members 25 and 26 together in a conveniently adjustable and releasable way. Other means are available which are equivalent to, and may readily be substituted for, whisker-like projections 27, 28 to achieve the adjustable and releasable fastening function thereof. For example, cooperating VELCRO® fastener strips could be applied to the superior surface of loop member 25 and to the inferior surface of loop member 26, in lieu of whisker-like projections. For another example, a strip coated on both sides with a pressure-sensitive adhesive could be applied to the superior surface of loop member 25, or to the inferior surface of loop member 26, or to both surfaces, in lieu of whisker-like projections. Such adhesive strips are readily obtainable in the market. For instance, tape with pressure-sensitive adhesive on both sides, and flat, rectangular patches coated on both sides with pressure-sensitive adhesive, are widely available under brands including the SCOTCH® brand. These and virtually any like material could readily be adapted, by a person skilled in the art, to provide the desired adjustable and releasable fastening means.

FIG. 5 shows an alternative embodiment of an adjustable and easily releasable plunger loop. It is preferably made of a resilient, elastomeric plastic and is preferably molded of a single piece with the plunger shaft 23, although it can be made separately and affixed at the proximal end of the shaft 23 by conventional means such as gluing, cementing or heat bonding. If desired, a plunger button 24 (not shown in FIG. 5 but indicated in FIGS. 1 and 3) can be provided in association with the plunger loop. The plunger loop of FIG. 5 comprises an inferior loop member 40 and a superior loop member 41 which are biased to return to their resting state, as shown, and to form a loop which defines an aperture through which a thumb or finger can be inserted. Preferably the diameter of the aperture thus defined is, in the loop members' resting state, small enough to fit snugly a small adult index finger. When the operator's thumb or finger is inserted into the aperture, loop members 40 and 41 are displaced in a manner that expands the aperture to accommodate the thumb or finger; but because the loop members are biased to return to their resting state, they exert springing forces which hold the finger or thumb securely, and the plunger loop they form resists opening and prevents escape of the thumb or finger during performance of the upward (aspiration) stroke of the plunger. When the injection procedure is complete, the thumb or finger is released simply by withdrawing it from the loop.

It will be appreciated that whereas the embodiment of the adjustable plunger loop shown in FIGS. 3 and 4 employs whisker-like projections 27, 28 to provide adjustability of the loop and resistance against opening during the aspiration step, the embodiment of FIG. 5 depends principally on the springing forces exerted by loop members 40 and 41 to accomplish these purposes.

Another alternative adjustable plunger loop structure is illustrated in FIG. 1, where loop members 30 and 31, preferably formed integrally with plunger button 24, are generally configured as overlapping arcs of a circle when in their resting state. Loop members 30 and 31 are made of a resilient material, biased to return to their resting state after a load is withdrawn. In their resting state, loop members 30 and 31 define an aperture that is preferably no larger than a small adult index finger. When an index finger or thumb that is larger than the aperture is attempted to be inserted therein, loop members 30 and 31 are displaced sufficiently to accommodate the finger or thumb; but because they are biased to return to their resting state, they exert a springing force upon the finger or thumb, embracing it snugly. When the thumb or finger so embraced is then lifted to exert a withdrawing force upon the plunger, loop members 30 and 31 retain it, enabling the accomplishment of the aspiration test. After that test, or the injection procedure, is complete, the thumb or finger may be withdrawn. Loop members 30 and 31 in the embodiment shown in FIG. 1 thus act similarly to loop members 40 and 41 in the embodiment shown in FIG. 5, a difference, however, being that loop members 40, 41 overlap in an "over-and-under" fashion while loop members 30 and 31 overlap in a "side-by-side" fashion.

It will be appreciated that a single-arm loop structure could be employed, instead of either the two-overlapping-loop-members structure described above and shown in FIG. 1 or the two-overlapping-loop-members structure described above and shown in FIG. 5. Such a single-arm loop structure is shown in FIG. 6, where single loop member 50 defines an aperture open at one side, rather than aperture closed on all sides. Loop member 50 is preferably molded integrally with, but may be formed separately and affixed at the proximal end of, plunger shaft 23. If desired, a plunger button 24 (not shown in FIG. 6 but indicated in FIGS. 1 and 3) may be provided in association with loop member 50. Loop member 50 is preferably made of a resilient, elastomeric plastic and it preferably forms an aperture which, in the resting configuration shown in FIG. 6, has a diameter not larger than that of a small adult index finger. When the operator's thumb or finger is inserted into the aperture, loop member 50 is displaced to accommodate that thumb or finger; but because loop member 50 is biased to return to its resting configuration, it captures and snugly holds the finger or thumb and resists further opening when the finger or thumb is raised to perform the upward (aspiration) stroke. Loop member 50 is preferably provided, at the free end thereof, with a detent 51 which serves to prevent escape of the thumb or finger from the open side of the aperture when the loop is under load, as when the captured finger or thumb is being used to apply a plunger-withdrawing force.

Figure 8:
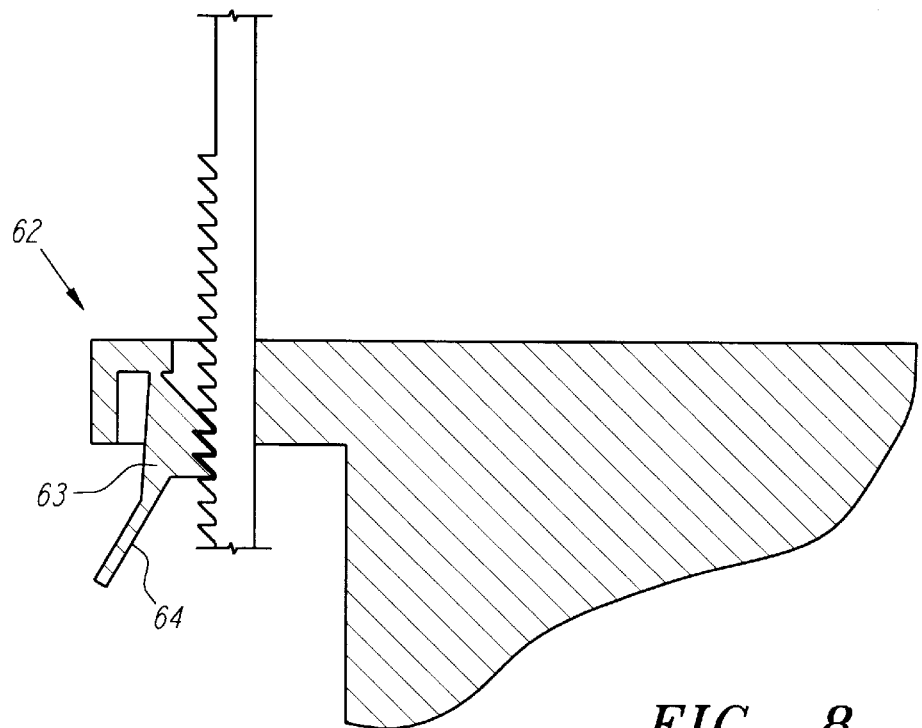
FIG. 8 is a cross-sectional view, taken though the ratchet housing of FIG. 7, which illustrates the cooperation between the teeth on the outer surface of the free end of the loop which passes through the ratchet housing and the teeth on a pawl which is movably mounted within the ratchet housing.

Yet another alternative for constructing an adjustable plunger loop is shown in FIGS. 7 and 8. Single loop member 60 is made of a flexible material, preferably a plastic, and is fixed at one end to the proximal end of plunger shaft 23. It is preferably molded of a single piece with the plunger shaft, although it can be formed separately and attached to the plunger shaft by conventional means. Loop member 60 may, if desired, be provided in association with a plunger button 24 (not shown in FIGS. 7 and 8, but indicated in FIGS. 1 and 3). At least the portion near the free (distal) end of loop member 60 has upon its superior surface, and preferably formed integrally therewith, a series of sawtooth projections 61. Ratchet housing 62 is preferably molded integrally with plunger shaft 23 but may be formed separately and attached by conventional means. When the free end of loop member 60 is conducted through ratchet housing 62, a closed loop is formed through which the operator's thumb or finger may be inserted.

Ratchet housing 62 is provided with a pawl 63 which comprises one or more sawtooth projections configured to mesh with those on loop member 60. Preferably, pawl 63 is also provided with a releasing tang 64. Pawl 63 is pivotably mounted within the ratchet housing and is biased to contact loop member 60 so that the sawtooth projections on loop member 60 mesh with one or more sawtooth projections on the pawl. Preferably the mounting of the pawl, and its bias to engage the sawtooth projections on the loop member, are accomplished by making the pawl of a flexible material and forming it integrally with the ratchet housing.

It will be appreciated that the cooperation of the loop member 60 with the pawl 63 provides a snare-like action, such that the loop can be easily adjusted to make the aperture smaller and tighten it around a finger or thumb which is inserted therethrough, but the loop resists opening under load. The tightening adjustment is accomplished by pushing or pulling the free end of the loop member 60 farther through the ratchet housing 62. The pivotably mounted pawl rides over the sawtooth projections on the loop member and permits its passage so as to decrease the size of the aperture; but when a withdrawing force is applied, the sawtooth projections on the loop member engage with one or more corresponding projections on the pawl and resist the enlargement of the loop aperture.

After the injection procedure (or the use of the syringe in a venous catheter-insertion procedure) has been completed, the operator may simply withdraw the finger or thumb from the aperture. Alternatively, the pawl may be provided with a tang 64 which affords the operator a convenient means to disengage the pawl from the loop member so as to permit the latter's withdrawal from the ratchet housing and the enlargement of the plunger loop so as to facilitate withdrawal of the operator's finger or thumb.

It is within the skill of the art to devise a snare-like loop-size adjustment means which is simpler than that shown in FIGS. 7 and 8 but which will still work adequately for the purpose. For example, it is possible to dispense with the pivotably-mounted pawl and use instead a single ratchet tooth, mounted in or formed integrally with the roof (that is, the side facing sawtooth projections 61) of the ratchet housing 62, and to dimension the ratchet housing and tooth so that the tooth engages the sawtooth projections 61 on the loop member 60. By varying the flexibility if the materials, or by varying the pitch of the ratchet tooth and the sawtooth projections 61 or the dimensions thereof, or the degree of interference therebetween, practitioners of skill in the art can readily arrive at a configuration which affords acceptable ease of closing the loop and an acceptable amount of resistance by the loop against opening under load. If both great ease of closing the loop and high resistance to opening are desired, the pitch of the sawtooth projections 61 and the ratchet tooth can be varied so that the pitch of the proximally-facing (i.e., toward the fixed end, and away from the free end, of loop member 60), sides of the sawtooth projections on the loop member 60 is much steeper than the pitch of the distally-facing (i.e., toward the free end of loop member 60) sides thereof. It will be appreciated that if the projections on the loop member are so configured they will cooperate with the ratchet tooth to provide a snare-like loop size adjustment means, in that the loop may easily be tightened by pulling on the distal end of loop member 60 to conduct it through ratchet housing 62, but may not easily be loosened. Thus the finger or thumb T may be secured snugly within the aperture defined by the loop member and may be withdrawn from the aperture thereafter without loosening it; or, by applying sufficient force, the loop member may be made to withdraw partially from the ratchet housing so that the plunger loop loosens to facilitate withdrawal of the finger or thumb.

As will be evident from the foregoing description, a practitioner using the syringe here disclosed for the injection of medicaments can easily and conveniently perform the aspiration test with a single hand, by performing the following steps: First the practitioner picks up the syringe by grasping the barrel between thumb and middle finger as shown in FIG. 11 (or, if preferred, between index and middle fingers as shown in FIG. 10) in the region of the finger-stop structures. Next, the practitioner inserts the index finger (if the thumb is being used to grasp the barrel) or the thumb (if the index finger is being used to grasp the barrel) through the loop aperture. Next, the aperture is adjusted if necessary, as described above, to secure the plunger-operating finger (or thumb) snugly within it. The practitioner then loads the medicament into the syringe, measuring its amount with the syringe's calibration scale if desired. Using one hand to stabilize the patient's arm (or other injection site), the practitioner then inserts the needle with the other hand. Because the plunger-operating finger (or thumb) is secured within the adjustable loop aperture atop the syringe's plunger member while the barrel is being securely grasped by other fingers of the same hand through the use of the finger-stops, the practitioner can easily draw the plunger backward to perform the aspiration test simply by raising the plunger-operating finger or thumb. If the test indicates that a blood vessel has been punctured, and intravenous injection of the medicament is not desired, then the practitioner withdraws the needle and starts over; but if a blood vessel has not been punctured, then the practitioner proceeds with the injection in the usual way.

A practitioner who desires to insert a catheter or tube into the lumen of a blood vessel can manipulate the syringe here disclosed in a similar manner, so far as the techniques of grasping the syringe barrel and engaging the plunger-operating finger or thumb with the plunger are concerned.

The present invention may be embodied in other specific forms without departing from the spirit or essential characteristics thereof. The presently disclosed embodiments are therefore to be considered in all respects as being examples only, the scope of the invention being indicated by the appended claims rather than by the foregoing description, and all changes which come within the meaning and range of equivalency of the claims are therefore intended to be embraced therein.

What is claimed is:

1. A hypodermic syringe comprising a barrel and plunger, said plunger slidably mounted in said barrel and having an end extending from said barrel, and an aperture-forming means on said plunger end, said aperture-forming means being adjustable in aperture size for accommodating different sizes of fingers and thumbs and having means for accommodating finger and thumb forces in a direction for withdrawing said plunger from said barrel.

2. A hypodermic syringe of claim 1 wherein said barrel includes dual-directional finger-stop means on diametrically opposed sides of said barrel.

3. A hypodermic syringe of claim 1 wherein said barrel further comprises a pair of dual-directional finger-stops on radially opposite positions upon said barrel, said stops being less than fully circumferential about said barrel.

4. A hypodermic syringe comprising:

a barrel;

a plunger, slidably mounted in said barrel and having an end extending from said barrel; and an aperture-forming means on said plunger end, said aperture-forming means being fashioned of a resilient flexible material such that said aperture-forming means self-adjusts in aperture size by expanding to accommodate different sizes of fingers and thumbs in response to the insertion of such fingers and thumbs into said aperture-forming means.

* * * * *